US00PP30604P2

(12) United States Plant Patent
Smith

(10) Patent No.: US PP30,604 P2
(45) Date of Patent: Jun. 25, 2019

(54) ***CHRYSANTHEMUM* PLANT NAMED 'CIFZ0072'**

(50) Latin Name: ***Chrysanthemum* x *morifolium***
Varietal Denomination: CIFZ0072

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/998,080

(22) Filed: Jun. 26, 2018

(51) Int. Cl.
*A01H 5/02* (2018.01)

(52) U.S. Cl.
USPC ..... Plt./286

(58) Field of Classification Search
USPC ..... Plt./263.1, 284, 286
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new garden type *Chrysanthemum* plant named 'CIFZ0072' particularly distinguished by the medium size plant with round mound plant habit, a medium size anemone flower with bicolor red petals with yellow base and orange-bronze disk that becomes more yellow with age, and a natural season response in late September/early October.

1 Drawing Sheet

Figure 1:
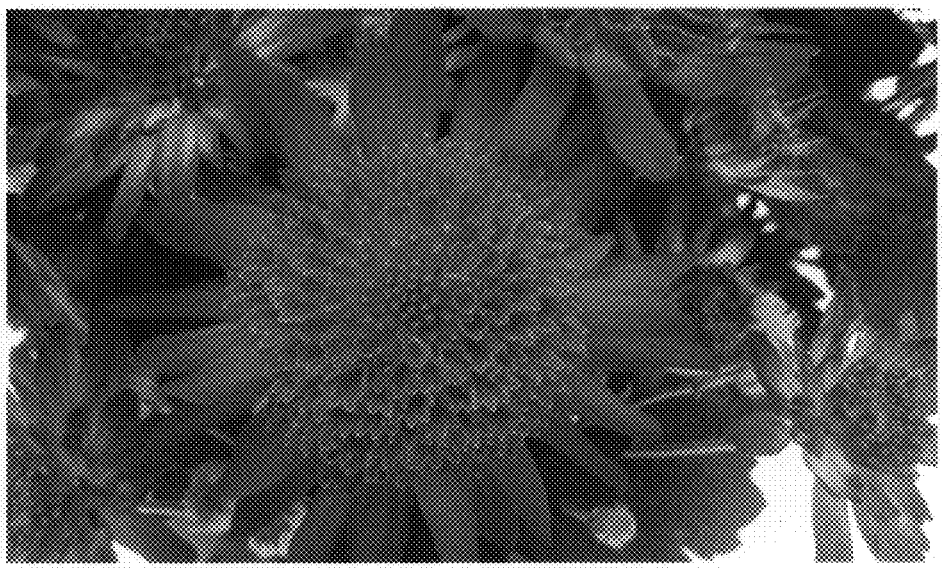

Latin name of the genus and species of the plant claimed: *Chrysanthemum* x *morifolium*.

Varietal denomination: 'CIFZ0072'.

BACKGROUND OF THE NEW PLANT

The present invention comprises a new *Chrysanthemum*, botanically known as *Chrysanthemum* x *morifolium*, and hereinafter referred to by the variety name 'CIFZ0072'.

'CIFZ0072' is a product of a planned breeding program. The new cultivar has a medium size plant with round mound plant habit, a medium size anemone flower with bicolor red petals with yellow base and orange-bronze disk that becomes more yellow with age, and a natural season response in late September/early October.

'CIFZ0072' originated from a cross made in the spring of 2014 in Enkhuizen, The Netherlands. Seeds were sown in June 2014 in Gilroy, Calif. and 'CIFZ0072' was selected from the resulting population on Nov. 7, 2014 in Monroeville, N.J.

The female parent was an unnamed, unpatented, selection from own breeding code '10-M061'. When compared to the female parent, 'CIFZ0072' has:

1. Similar flower type and size but red not orange ray florets and more of a bicolor effect than the female parent.
2. Blackcloth response is similar but natural season response is two weeks slower than the female parent.
3. Sturdier plant that is less apt to split than the female parent.
4. Similar plant habit and overall size as the female parent.

The male parent was an unnamed, unpatented, selection from own breeding code '09-M178'. When compared to the male parent, 'CIFZ0072' has:

1. Slightly smaller flower size with anemone flower not daisy flower type like the male parent, and red/bronze/yellow flower color not dark pink/white flower color of the male parent.

2. Blackcloth response is similar but natural season response is three weeks slower than the male parent.
3. Similar plant habit but larger overall plant size than the male parent.
4. Flowers more uniform thank the male parent.

The first act of asexual reproduction of 'CIFZ0072' was accomplished when vegetative cuttings were propagated from the initial selection in January 2015 in Mebane, N.C.

BRIEF SUMMARY OF INVENTION

Horticultural examination of plants grown from cuttings of the plant initiated in January 2015 and continuing thereafter, has demonstrated that the combination of characteristics as herein disclosed for 'CIFZ0072' are firmly fixed and are retained through successive generations of asexual reproduction.

'CIFZ0072' has not been observed under all possible environmental conditions. The phenotype may vary significantly with variations in environment such as temperature, light intensity and day length.

A Plant Breeder's Right for this cultivar has not yet been applied for. 'CIFZ0072' has not been made publicly available prior to the effective filing date of this application, notwithstanding any disclosure that may have been made less than one year prior to the effective filing date of this application by the inventor or another who obtained 'CIFZ0072' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0072' with colors being as true as possible with an illustration of this type.

Figure 2:
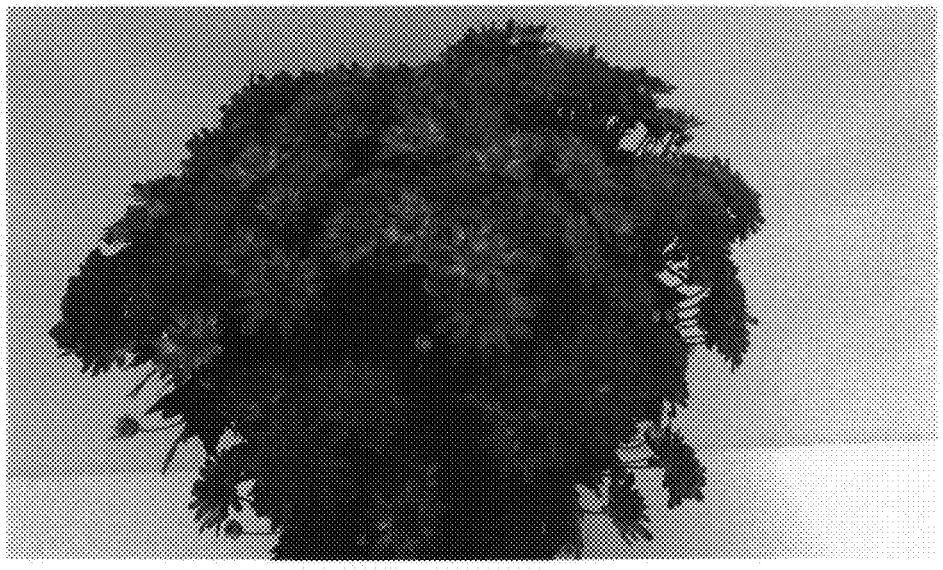

The photographic drawings show in FIG. 1 a close view of flower of the new variety and in FIG. 2 a flowering plant from an indoor blackcloth trial.

The aforementioned photographs: FIG. 1, as well as FIG. 2, were taken in April 2018 both showing a plant from the same blackcloth indoor trial in Gilroy, Calif.

These plants were about 11 weeks of age. One rooted cutting per pot had been planted in an eight-inch pot, not pinched in week 5, and black clothed from week 7. Plants started flowering in April.

DETAILED BOTANICAL DESCRIPTION

The measurements were taken in Gilroy, Calif. in April 2018 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0072 AND 'SYEDA REDDA':

| | 'CIFZ0072' | 'Syeda Redda'(U.S. Plant Pat. No. 22,835) |
|---|---|---|
| Flowering response (blackcloth): | One week slower | One week faster |
| Flowering response (natural): | Similar or up to one week slower when hot | Similar or up to one weekfaster when hot |
| Flower color: | Bi-color red/yellow ray florets | Solid red ray florets |
| Flower type: | Anemone - larger, raised disc florets | Daisy - smaller, flatter disk florets |
| Flower size: | Bit larger | Bit smaller |
| Plants, stems, sturdiness: | Sturdier, less apt to split | Less sturdy, more apt to split |
| Plant habit or size: | Larger overall size with more mounded plant habit | Smaller plant size with more sphere plant habit |

TABLE 2

DIFFERENCES BETWEEN THE NEW VARIETY 'CIFZ0072' AND 'FAME RED':

| | 'CIFZ0072' | 'Fame Red' (Unpatented) |
|---|---|---|
| Flowering response (blackcloth): | Unknown, likely slower | Unknown, likely faster |
| Flowering response (natural): | Two weeks slower | Two weeks faster |
| Flower color: | Bi-color red/yellow ray florets | Solid red ray florets |
| Flower type: | Anemone - larger, raised disk florets | Daisy - smaller, flatter disk florets |
| Flower size: | Larger | Smaller |
| Plant habit or size: | Similar or bit larger | Similar or bit smaller |

Plant:

*Form, growth and habit.*—Herbaceous garden-type, stems upright and outwardly spreading, freely branching, strong and moderately vigorous growth habit.

*Plant height* (*above soil*).—Average of 22.5 cm.

*Plant height* (*inflorescence included*).—Average of 28 cm.

*Plant width.*—Average of 38.5 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B but whiter.

Foliage:

*Arrangement.*—Alternate.

*Immature leaf, color upper surface.*—RHS 137A.

*Immature leaf, color lower surface.*—RHS 137B.

*Mature leaf, color, upper surface.*—RHS 137A.

*Mature leaf, color lower surface.*—RHS 137B.

*Length.*—Average of 6.2 cm.

*Width.*—Average of 5 cm.

*Shape.*—Oval.

*Base shape.*—Truncate.

*Apex shape.*—Macronate.

*Margin.*—2 main lobes, serrulate.

*Texture, upper surface.*—Small hairs.

*Texture, lower surface.*—Small hairs.

*Color of veins, upper surface.*—RHS 144B.

*Color of veins, lower surface.*—RHS 144B.

*Pattern of veining.*—Palmate.

*Petiole color.*—RHS 144B.

*Petiole length.*—Average of 1.5 cm.

*Diameter.*—Average of 0.3 cm.

*Texture.*—Small hairs.

Stem:

*Quantity of main branches per plant.*—Average of 8.

*Color of stem.*—RHS 137B.

*Length of stem.*—About 15 cm.

*Diameter.*—Average of 0.3 cm.

*Length of internodes.*—Average of 1.2 cm.

*Texture.*—Covered with Bifid hairs.

*Color of peduncle.*—RHS 141B.

*Length of peduncle.*—Average of 4.7 cm.

*Peduncle diameter.*—Average of 0.1 cm.

*Texture.*—Covered with hairs.

Inflorescence:

*Type.*—Compositae, solitary, anemone type inflorescences borne terminally above foliage, ray and disc florets arranged on a capitulum.

*Quantity of short days to flowering* (*response time*).—Approximately 8 weeks.

*Natural season flowering.*—Late September/Early October.

*Quantity of inflorescences per plant.*—168 plus buds that are yet to show color.

*Lastingness of individual blooms on the plant.*—About five weeks from first color.

*Fragrance.*—Slightly spicy.

Bud (when showing color):

*Color.*—Top of emerging ray floret=RHS 46A; Bottom of emerging ray floret=RHS 1B.

*Length.*—1.0 cm.

*Width.*—1.1 cm.

*Shape.*—Prolate.

Immature inflorescence:

*Diameter.*—Average of 3.9 cm.

*Color of ray florets, upper surface.*—RHS 53A fading to RHS 3A.

*Color of ray florets, lower surface.*—RHS 46A fading to RHS 3A.

Mature inflorescence:

*Diameter.*—Average of 6.0 cm.

*Depth.*—Average of 1.5 cm.

*Total diameter of disc.*—Average of 3.5 cm.

*Receptacle color*.—RHS 145B.
*Receptacle height*.—Average of 0.3 cm.
*Receptacle diameter*.—Average of 0.3 cm.

Ray florets:
*Average quantity of florets*.—32.
*Color of florets, upper surface* (*abaxial*).—RHS 53A.
*Color inner surface* (*adaxial*).—RHS 46A fading to RHS 3D.
*Length*.—Average of 2.5 cm.
*Width/diameter*.—Average of 0.7 cm.
*Shape*.—Oblong to elliptical.
*Apex shape*.—Emarginate.
*Base shape*.—Cuneate.
*Margin*.—Entire.
*Texture, upper surface*.—Smooth.
*Lower surface*.—Smooth.

Disc florets:
*Average quantity of florets*.—140.
*Width*.—Average of 0.2 cm.
*Length*.—Average of 0.6 cm.
*Color*.—RHS 46A.
*Shape*.—Tubular, elongated.
*Apex shape*.—Acute, 5 pointed.

Phyllaries:
*Quantity*.—Average of 18.
*Color, upper surface*.—RHS 137D.
*Color, lower surface*.—RHS 137B.
*Length*.—Average of 0.7 cm.
*Width*.—Average of 0.2 cm.
*Shape*.—Lanceolate.
*Apex shape*.—Acute.
*Base*.—Fused.
*Margins*.—Entire.
*Texture, upper surface*.—Smooth.
*Texture, lower surface*.—Hairs.

Reproductive organs:
*Pistil*.—One, found on both types of florets.
*Length*.—Average of 0.4 cm.
*Style color*.—RHS 1C.
*Style length*.—Average of 0.3 cm.
*Stigma color*.—RHS 46A.
*Stigma shape*.—Bi-lobed.
*Ovary color*.—RHS 1D.
*Ovary length*.—Average of 0.1 cm.
*Ovary width*.—Average of 0.1 cm.

Androecium:
*Stamens*.—No apparent male parts.
*Color of filaments*.—N/a.
*Length filaments*.—N/a.
*Anther color*.—N/a.
*Anther length*.—N/a.
*Anther shape*.—N/a.
*Color of pollen*.—N/a.
*Pollen amount*.—N/a.
*Fertility/seed set*.—Has not been determined to date.
*Disease/pest resistance*.—Has not been determined to date.

What is claimed is:

1. A new and distinct variety of *Chrysanthemum* plant named 'CIFZ0072' substantially as illustrated and described herein.

* * * * *